United States Patent [19]

Hunt

[11] Patent Number: 4,957,905

[45] Date of Patent: Sep. 18, 1990

[54] 9-(N'-SUBSTITUTED HYDRAZONE) DERIVATIVES OF ERYTHROMYCINS

[75] Inventor: Eric Hunt, Betchworth, England

[73] Assignee: Beecham Group p.l.c., England

[21] Appl. No.: 241,902

[22] Filed: Sep. 7, 1988

[30] Foreign Application Priority Data

Sep. 9, 1987 [GB] United Kingdom ............... 8721165

[51] Int. Cl.$^5$ ..................... A61K 31/70; C07H 17/08
[52] U.S. Cl. ..................................... 514/29; 536/7.2; 536/7.4
[58] Field of Search ..................... 536/7.2, 7.4; 514/29

[56] References Cited

U.S. PATENT DOCUMENTS 4,680,386 7/1987 Morimoto et al. ................... 536/7.4

OTHER PUBLICATIONS

Morrison et al., Organic Chemistry, 3rd ed, 1979, p. 632.

Primary Examiner—Johnnie R. Brown
Assistant Examiner—Elli Peselev
Attorney, Agent, or Firm—Jacobs & Jacobs

[57] ABSTRACT 9-(N'-substituted hydrazone) derivatives of certain erythromycin compounds are novel, antibacterially active compounds which can be prepared by treatment of the corresponding 9-imine derivative with an N'-substituted hydrazine.

15 Claims, No Drawings

9-(N'-SUBSTITUTED HYDRAZONE) DERIVATIVES OF ERYTHROMYCINS

The present invention relates to novel chemical compounds, their preparation and their use, and in particular to a novel class of erythromycin derivatives. These compounds have antibacterial properties, in particular against Gram-positive bacteria but also against some Gram-negative bacteria, and they are therefore of use in the treatment of bacterial infections in humans and animals caused by a wide range of organisms.

Erythromycin was first described in U.S. Pat. No. 2,653,899 (R. L. Bunch et al; Eli Lilly). The structure of erythromycins can be represented as follows:

in which
$R^a$ denotes hydrogen or hydroxy and
$R^b$ denotes hydrogen or methyl.

The basic erythromycin structure comprises:
(i) a 14-membered lactone ring, referred to as the erythronolide ring, numbered with unprimed digits as shown in the above formula,
(ii) a first sugar ring, known as the desosamine ring, numbered with single-primed digits, and
(iii) a second sugar ring, known as the cladinose ring, numbered with double-primed digits.

The erythronolide ring can exist in two forms:
erythronolide A (in which $R^a$=OH)
erythronolide B (in which $R^a$=H).

The four main naturally occurring erythromycins are as follows:

| Erythromycin | $R^a$ | $R^b$ |
|---|---|---|
| A | OH | $CH_3$ |
| B | H | $CH_3$ |
| C | OH | H |
| D | H | H | of which erythromycin A is by far the most important.

Erythromycins, and in particular erythromycin A, are antibiotics widely employed clinically in the treatment of infections caused by Gram-positive and some Gram-negative bacteria. A major drawback of erythromycins is their poor acid stability, resulting in poor and erratic oral absorption.

Numerous attempts have been made to modify erythromycin to produce derivatives having improved acid stability without loss of the antibacterial activity.

Among the many erythromycin derivatives that have been described in the literature is erythromycin A 9-hydrazone, prepared by reaction of erythromycin A with anhydrous hydrazine in anhydrous methanol in the course of early degradation studies on erythromycin (M. V. Sigal, Jr., et al, *J. Amer. Chem. Soc.* 78, 388–395 (1956)). Erythromycin A 9-hydrazone and its N'-isopropylidine derivative have also been mentioned as intermediates in the preparation of erythromycylamine by catalytic hydrogenation (E.H. Massey et al, *Tetrahedron Letters* No. 2, 157–160, 1970).

The reaction of erythrocmycin A or B 9-hydrazone with an aldehyde or ketone to give various antimicrobially active erythromycin azine derivatives of the formula $$E=N-N=C\begin{matrix}R'\\|\\R''\end{matrix}$$

(in which E denotes the 9-deoxyerythromycin A or B nucleus, and R' and R" variously denote hydrogen, alkyl, etc. as more particularly defined in the reference) has been described in U.S. Pat. No. 3,780,020 (D. Evans, Lilly).

Classically, hydrazones are prepared by the reaction of a hydrazine with a carbonyl compound, but the 9-keto group of erythromycin reacts only sluggishly with hydrazine itself and does not react with substituted hydrazines such as phenyl hydrazine and semicarbazide (M. V. Sigal, Jr., op. cit.).

It has now been found that substituted hydrazones of erythromycin can be prepared from erythromycin 9-imine (instead of from the 9-keto compound), that route provides access to various novel substituted hydrazone derivatives of erythromycin, and that such derivatives have antibacterial activity.

The present invention provides various novel, antibacterially active, N'-substituted derivatives of erythromycin 9-hydrazone.

In particular, the present invention provides a compound of the general formula I or a pharmaceutically acceptable ester or acid addition salt thereof:

wherein
$R^1$ denotes a hydrogen atom or an alkyl group having up to 6 carbon atoms;
$R^2$ denotes an unsubstituted or substituted alkyl group, an unsubstituted or substituted aryl group, an unsubstituted or substituted heterocyclyl group, or a carbamoyl group;
$R^3$ denotes a hydrogen atom;
$R^4$ denotes a hydrogen atom or a hydroxy group; or
$R^1$ and $R^2$ together denote a straight-chain alkylene or alkenylene group having from 3 to 6 carbon atoms; or
$R^1$ and $R^3$ together denote a methylene group which may be unsubstituted or substituted by an unsubstituted or substituted hydrocarbon group or by an unsubstituted or substituted heterocyclyl group; or $OR^3$ and $R^4$ together denote a carbonate group; and $R^7$ denotes hydrogen or methyl;

one of $R^8$ and $R^9$ denotes hydrogen, hydroxy, alkoxy, alkanoyloxy, amino, substituted amino, or a group of the formula $R^A$—$SO_2$—O—, in which $R^A$ denotes an organic group, and the other of $R^8$ and $R^9$ denotes hydrogen, or $R^8$ and $R^9$ together denote an oxo group, an oxime group, or a substituted oxime group.

The term 'hydrocarbon' as used herein includes groups having up to 18 carbon atoms, suitably up to 10 carbon atoms, conveniently up to 6 carbon atoms. Suitable hydrocarbon groups include $(C_{1-6})$alkyl, $(C_{2-6})$alkenyl, $(C_{2-6})$alkynyl, $(C_{3-7})$cycloalkyl, aryl, $(C_{3-7})$cycloalkyl$(C_{1-6})$alkyl, aryl$(C_{1-6})$alkyl, $(C_{1-6})$alkyl$(C_{3-7})$cycloalkyl, and $(C_{1-6})$alkylaryl.

Examples of suitable optional substituents for the above-mentioned hydrocarbon groups include, heterocyclyl, amino, $(C_{1-6})$alkanoylamino, (mono, di, or tri)-$(C_{1-6})$alkylamino, hydroxy, $(C_{1-6})$alkoxy, mercapto, $(C_{1-6})$alkylthio, heterocyclylthio, arylthio, sulphamoyl, carbamoyl, amidino, guanidino, nitro, chloro, bromo, fluoro, carboxy and salts and esters thereof, $(C_{1-6})$alkanoyloxy, arylcarbonyloxy, heterocyclylcarbonyl and acyl groups. Any alkyl group or moiety referred to herein may be straight or branched, unsubstituted or substituted, and may contain, for example, up to 12 carbon atoms, suitably up to 6 carbon atoms. In particular, the alkyl group or moiety may be an unsubstituted or substituted methyl, ethyl, n-propyl, iso-propyl, n-butyl, sec-butyl, isobutyl or tert-butyl group. Examples of suitable optional substitutents for any such alkyl group or moiety include the above-listed substitutents for hydrocarbon groups, and also the above-listed non-alkyl hydrocarbon groups, for example $(C_{2-6})$alkenyl and aryl groups.

The term 'aryl' as used herein includes phenyl and naphthyl, which may be unsubstituted or substituted by up to five, preferably up to three, groups selected from the above-listed substituents for hydrocarbon groups, and the above-listed hydrocarbon groups, including, for example, substituents selected from halogen, $(C_{1-6})$alkyl, phenyl, $(C_{1-6})$alkoxy, halo$(C_{1-6})$alkyl, hydroxy, amino, nitro, carboxy, $(C_{1-6})$alkoxycarbonyl, $(C_{1-6})$alkoxycarbonyl$(C_{1-6})$alkyl, $(C_{1-6})$alkanoyloxy, and $(C_{1-6})$alkanoyl groups.

The term 'acyl' as used herein includes formyl, unsubstituted and substituted hydrocarbon-carbonyl and hydrocarbonoxy-carbonyl groups, including, for example, unsubstituted and substituted alkanoyl, cycloalkylcarbonyl, arylcarbonyl, alkoxycarbonyl, aryloxycarbonyl, and heterocyclylcarbonyl groups. The term 'acyloxy' is used analogously.

The term 'heterocyclyl' and 'heterocyclic' as used herein include aromatic and non-aromatic, single and fused, rings, suitably containing up to four hetero-atoms in each ring selected from oxygen, nitrogen and sulphur, which rings may be unsubstituted or substituted by, for example, up to three groups selected from halogen, $(C_{1-6})$alkyl, $(C_{1-6})$alkoxy, halo$(C_{1-6})$alkyl, hydroxy, amino, carboxy, carboxy salts, carboxy esters, $(C_{1-6})$alkoxycarbonyl, $(C_{1-6})$alkoxycarbonyl $(C_{1-6})$alkyl, aryl, and oxo groups. Each heterocyclic ring suitably has from 4 to 7, preferably 5 or 6, ring atoms. A fused heterocyclic ring system may include carbocyclic rings and need include only one heterocyclic ring.

The erythromycin derivatives according to the invention are characterised by an N'-substituted hydrazone substituent in the 9-position, which may optionally combine with the 11-hydroxy group to give a 9-N,11-O-cyclic derivative.

The N'-substituent denoted by $R^1$ is a hydrogen atom or a $(C_{1-6})$alkyl group, preferably a methyl group.

The N'-substitutent denoted by $R^2$ may be an alkyl, aryl, or heterocyclyl group, each of which may be substituted, or a carbamoyl group —$CONH_2$.

An alkyl group $R^2$ is advantageously a $(C_{1-6})$alkyl group, which may optionally be substituted. Examples of suitable alkyl groups $R^2$ include methyl and β-hydroxyethyl groups.

An aryl group $R^2$ is advantageously a phenyl group, which may optionally be substituted.

A heterocyclyl group $R^2$ may be an aromatic or non-aromatic heterocyclyl group. Advantageously it is a N-containing heterocyclyl group. Advantageously it is a 5- or 6-membered heterocyclyl group. An example of a suitable heterocyclyl group is the pyridyl group.

$R^1$ and $R^2$ may together denote a straight-chain $(C_{3-6})$alkylene or alkenylene group, such that $R^1$, $R^2$ and the nitrogen atom to which they are attached together denote a 4- to 7-membered, unsaturated or saturated, nitrogen-containing heterocyclyl group bonded to the remainder of the molecule through the nitrogen atom. An example of such a heterocyclyl group is the pyrrolidin-1-yl group, in which case $R^1$ and $R^2$ together denote a tetramethylene group.

$R^3$ may denote a hydrogen atom, as in naturally occurring erythromycins.

$R^1$ and $R^3$ may together denote a methylene group which may be unsubstituted or substituted by an unsubstituted or substituted hydrocarbon group or by an unsubstituted or substituted heterocyclyl group, such that a 9-N,11-O-cyclic derivative is formed with a 9,11-substituent of the formula

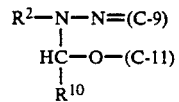

in which $R^2$ is defined as above and $R^{10}$ denotes hydrogen, an unsubstituted or substituted hydrocarbon group or an unsubstituted or substituted heterocyclyl group. Examples of suitable hydrocarbon groups $R^{10}$ include $(C_{1-6})$alkyl and aryl and of suitable heterocyclyl groups include furyl, pyranyl, thienyl, dihydropyranyl and tetrahydrofuryl. As a further alternative, the compound of the general formula I may contain an 11,12-carbonate group, in which case $OR^3$ and $R^4$ together denote a carbonate group:

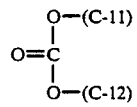

In the compounds of the general formula I, the 12-substituent denoted by $R^4$ is preferably a hydroxy group as in the erythronolide A ring, or, in other words, the compounds of the general formula I are preferably derivatives of erythromycin A. Alternatively, however, the present compounds may be derivatives of erythromycin B, in which case $R^4$ denotes a hydrogen atom, or of another naturally occurring erythromycin.

The —$OR^7$ group in the 3″-position of the cladinose ring may be a hydroxy group or a methoxy group. Preferably, $R^7$ denotes a methyl group as in erythromycin A.

The 4″-position of the cladinose ring may suitably carry a hydroxy group as in erythromycin A ($R^8$=H; $R^9$=OH). Various modifications of the 4″-position of the cladinose ring have previously been described and those modifications may be incorporated in the compounds according to the present invention:

(i) 4″-deoxy-4″-oxo derivatives ($R^8+R^9$=O) are described in U.S. Pat. Nos. 3,842,069 and 3,884,903, both P. H. Jones et al, Abbott Laboratories, and U.S. Pat. No. 4,150,220, F. C. Sciavolino, Pfizer;

(ii) 4″-epi-hydroxy derivatives ($R^8$=OH; $R^9$=H) and 4″-deoxy-4″-alkanoyloxy-4″-epi derivatives ($R^8$=alkanoyloxy, especially $CH_3COO$—; $R^9$=H) are described in U.S. Pat. No. 3,884,903, op cit., and U.S. Pat. No. 4,382,085, F. C. Sciavolino, Pfizer;

(iii) 4″-O-alkyl derivatives ($R^8$ or $R^9$=alkoxy, especially methoxy; the other of $R^8$ and $R^9$=H) are described in EP No. 0 080 818 A1, Taisho Pharmaceutical;

(iv) 4″-deoxy-4″-amino derivatives ($R^8$ or $R^9$=amino or substituted amino; the other of $R^8$ and $R^9$=H) are described in U.S. Pat. No. 4,150,220, op. cit.;

(v) 4″-deoxy-4″-oxime derivatives ($R^8+R^9$=oxime (=N-OH) or substituted oxime, especially acetyloxime (=N—O—CO—$CH_3$)) are also described in U.S. Pat. No. 4,150,220, op cit.;

(vi) 4″-O-sulphonyl derivatives ($R^8$=H, $R^9$=RA-$SO_2$-O-) are described in U.S. Pat. Nos. 3,836,519, 3,869,445 and 4,063,014, all R. Hallas et al. Abbott Laboratories;

(vii) 4″-deoxy derivatives ($R^8$=$R^9$=H) are described in JP No. 58-049396, Toyo Jozo KK.

In the 4″-deoxy-4″-(substituted amino) derivatives, the substituted amino group $R^8$ or $R^9$ may suitably be a group of the formula:

$-NHCOR^F$ or $-NHSO_2R^F$ in which $R^F$ denotes a hydrocarbon group.

In the 4″-O-sulphonyl derivatives, in which $R^8$ or $R^9$ denotes a sulphonyloxy group of the formula:

$R^A-SO_2-O-$, the organic group $R^A$ may suitably be an unsubstituted or substituted hydrocarbon, oxahydrocarbon, thiahydrocarbon or azahydrocarbon group, more especially an alkyl, alkenyl, unsubstituted or substituted aryl (especially phenyl, nitrophenyl, halophenyl or alkylphenyl), unsubstituted or substituted aralkyl (especially benzyl, nitrobenzyl, halobenzyl or alkylbenzyl), unsubstituted or substituted aryloxyalkyl (especially phenoxyalkyl, nitrophenoxyalkyl, halophenoxyalkyl or alkylphenoxyalkyl), or substituted ethyl (especially $R^G$—$CH_2$—$CH_2$—, wherein $R^G$ is defined as below) group.

Examples of groups $R^G$ in the 4″-substituent $R^G-CH_2-CH_2-SO_2-O-$ include amino, substituted amino, carbamoyl, substituted carbamoyl, sulphamoyl, substituted sulphamoyl, substituted ureido, substituted thioureido, alkoxy, alkythio, optionally substituted aryloxy, optionally substituted arylthio, optionally substituted benzyloxy, optionally substituted benzylthio, substituted suphonyl, substituted sulphinyl, substituted alkyl, substituted alkanoyl, substituted cyano, and other groups more specifically described in U.S. Pat. Nos. 3,869,445 and 4,063,014, op. cit.

Preferably, $R^A$ denotes a hydrocarbon group, particularly a ($C_{1-6}$)alkyl group, especially a methyl group.

The present invention includes pharmaceutically acceptable esters, especially in vivo hydrolysable esters, of the compounds of the general formula I. Such esters may be formed at any hydroxy group in the compounds of the general formula I, but usually the ester will be formed at the 2′-hydroxy group of the desosamine ring, thus giving a 2′-O-acyl derivative of the type described in U.S. Pat. No. 2,862,921 (R. E. Booth et al; Upjohn Co.), U.S. Pat. No. 2,993,833 (V.C. Stephens; Eli Lilly), U.S. Pat. No. 3,884,904 (P. H. Jones et al. Abbott Laboratories), U.S. Pat. Nos. 3,836,519, 3,842,069, 3,869,445, 3,884,903, and 4,150,220, all op. cit..

Suitable pharmaceutically acceptable in vivo hydrolysable esters include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic, and alkanedioic acids, in which each alkyl or alkenyl moiety advantageously has not more than 6 carbon atoms. Examples of particular esters include formates, acetates, propionates, butyrates, acrylates, and ethylsuccinates.

The present invention also includes acid addition salts, especially pharmaceutically acceptable acid addition salts, of the compounds of the general formula I. Such acid addition salts may, in particular, be formed at the 3′-dimethylamino group of the desosamine ring.

Various acid addition salts of erythromycin are described in U.S. Pat. No. 2,761,859 (C. E. Hoffhine, Jr.; Abbott Laboratories) and U.S. Pat. No. 2,852,429 (J. T. Shepler; Eli Lilly).

Suitable acid addition salts of the compounds of the invention include pharmaceutically acceptable inorganic acid addition salts, for example the sulphate, nitrate, phosphate, borate, hydrochloride and hydrobromide, and also pharmaceutically acceptable organic acid addition salts, for example the acetate, tartrate, maleate, citrate, succinate, benzoate, ascorbate, methane-sulphate, α-keto-glutarate, α-glycerophosphate, and glucose-1-phosphate. Preferably the acid addition salt is the laurylsulphate salt.

Examples of individual compounds according to the present invention include:

(i) erythromycin A 9-semicarbazone;
(ii) erythromycin A 9-phenylhydrazone;
(iii) erythromycin A 9-methylhydrazone;
(iv) erythromycin A 9-(2-hydroxyethyl)hydrazone;
(v) erythromycin A 9-tetramethylenehydrazone;
(vi) erythromycin A 9-(2-pyridyl)hydrazone;
(vii) erythromycin A 9-dimethylhydrazone;
(viii) 9-(Z)-erythromycin A 9-(N-methyl-N,11-O-methylene)hydrazone;
(ix) erythromycin A 9-[N-methyl-N-(2-hydroxyethyl)-]hydrazone;
(x) 9-(Z)-erythromycin A 9-[N-(2-hydroxyethyl)-N,11-O-methylene]hydrazone;
(xi) erythromycin A 9-dimethylhydrazone 11,12-carbonate;
(xii) 9-(Z)-erythromycin A 9-(N-methyl-N,11-O-methylene)hydrazone
(xiii) 9-(Z)-erythromycin A 9-(N-methyl-N,11-O-ethylidene)hydrazone
(xiv) erythromycin A 9-(N-methyl)-ethylhydrazone as well as corresponding derivatives in which the 4''-position is modified as discussed above;
and also
pharmaceutically acceptable esters and acid addition salts of such compounds.

The N'-monosubstituted 9-hydrazone derivatives according to the invention may be prepared by reacting an erythromycin A 9-imine, in which any reactive groups (other than the 9-imine group) may optionally be protected, with a substituted hydrazine; and thereafter if necessary carrying out one or more of the following steps:
(a) converting a substituent on the erythromycin structure to another such substituent in a conventional manner;
(b) removing any protecting groups; and
(c) forming a pharmaceutically acceptable ester or acid addition salt.

More particularly, a compound of the general formula I as hereinbefore defined or a pharmaceutically acceptable ester or acid addition salt thereof, may be prepared by a process which comprises reacting a compound of the general formula II:

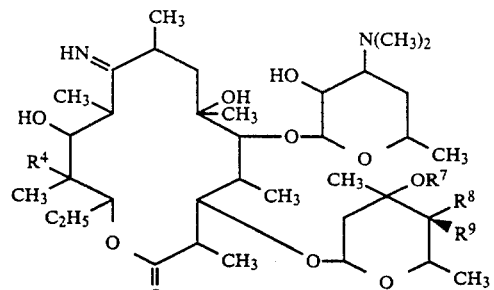

in which $R^4$, $R^7$, $R^8$ and $R^9$ are defined as above with respect to general formula I, and in which any reactive group (other than the 9-imine group) may optionally be protected, with a substituted hydrazine of the general formula III:

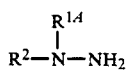

III in which
$R^{14}$ denotes a hydrogen atom, and
$R^2$ is defined as above with respect to general formula I, or
$R^{14}$ and $R^2$ together denote a straight-chain alkylene or alkenylene group having from 3 to 6 carbon atoms;
in the presence of an acid; to give a compound of the general formula IA:

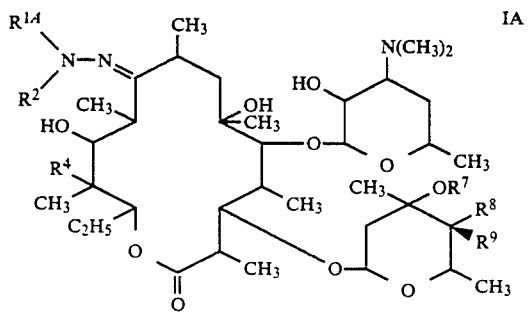

in which $R^{14}$, $R^2$, $R^4$, $R^7$, $R^8$ and $R^9$ are defined as above, and in which protecting groups may optionally be present; and thereafter, in any suitable order:
(a) if, in the desired compound of the general formula I, $R^1$ and $R^3$ together denote methylene which may be unsubstituted or substituted by an unsubstituted or substituted hydrocarbon group or an unsubstituted or substituted heterocyclyl group, reacting the compound of the general formula IA with:
(i) a compound of the general formula (IV):

$$R^{10}-CHO \qquad (IV)$$

in which $R^{10}$ is defined as above, or a reactive derivative thereof; or
(ii) a compound of the general formula (V):

in which $R^{10}$ is defined as above; and each of X and Y which may be identical or different, denotes a readily displaceable group,
to give a compound of the general formula IB:

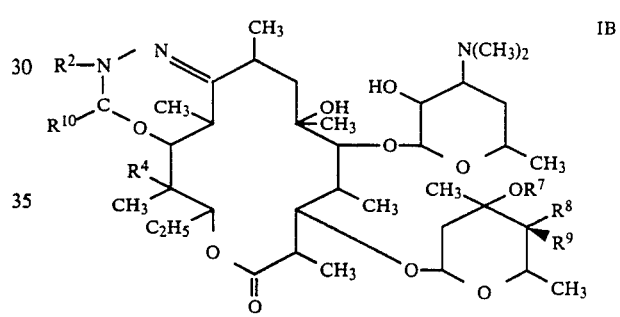

in which $R^2$, $R^4$, $R^7$, $R^8$, $R^9$ and $R^{10}$ are defined as above, and in which protecting groups may optionally be present;
(b) if, in the desired compound of the general formula I, $R^1$ denotes alkyl, subjecting the compound of the general formula IA above, or the compound of the general formula ID below in which $R^1$ denotes hydrogen, to a reductive alkylation to give a compound of the general formula IC:

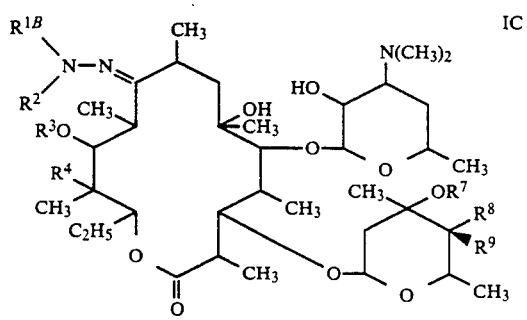

in which
$R^{1B}$ denotes an alkyl group having up to 6 carbon atoms,
$R^2$, $R^3$, $R^4$, $R^7$, $R^8$ and $R^9$ are defined as above, and in which protecting groups may optionally be present;

(c) if, in the desired compound of the general formula I, R³ and R⁴ together denote a carbonate group, reacting the compound of the general formula IA in which R⁴ denotes hydroxy, or the compound of the general formula IC in which R³ denotes hydrogen and R⁴ denotes hydroxy, with a reactive carbonyl compound, to give a compound of the general formula ID:

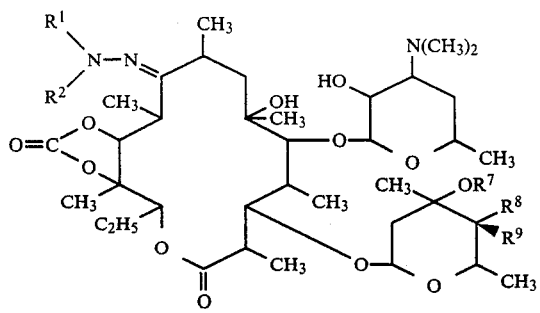

in which $R^1$, $R^2$, $R^7$, $R^8$ and $R^9$ are defined as above, and in which protecting groups may optionally be present;

(d) converting either or both of the groups denoted by $R^8$ and $R^9$ to another such group;

(e) removing any protecting group that may be present; and (f) forming a pharmaceutically acceptable ester or acid addition salt.

A compound of the general formula II in which:
each of $R^4$ and $R^9$ denotes hydroxy,
$R^7$ denotes methyl, and
$R^8$ denotes hydrogen,
is erythromycin A 9-imine, which may be prepared from erythromycin A via erythromycin A 9-oxime, by known methods, for example by the methods described in G. H. Timms et al. *Tetrahedron Letters* No.2, 195–198, 1971.

A compound of the general formula II in which:
each of $R^4$ and $R^8$ denotes hydrogen,
$R^7$ denotes methyl, and
$R^9$ denotes hydroxy,
is erythromycin B 9-imine, which may be prepared analogously from erythromycin B.

Other compounds of the general formula II may also be prepared, by methods known per se. from erythromycin A or another naturally occurring erythromycin. For example, a compound in which the 4"-position is substituted other than as in naturally-occurring erythromycins (that is to say, in which $R^8$ is other than hydrogen and/or $R^9$ is other than hydroxy) may be prepared as described in the respective references cited above.

In general, in the preparation of 9-imine compounds of the general formula II from erythromycin, the conversion of the 9-oxo group of erythromycin to a 9-imine group may be effected prior to or subsequent to modification of other positions of the erythromycin molecule.

Prior to carrying out the reaction of a compound of the general formula II with the substituted hydrazine of the general formula III, any reactive group of a compound of the general formula II (other than the 9-imine group) may optionally be protected in known manner although that has not in general been found to be necessary (except that, if $R^8$ and $R^9$ together denote an oxo group, that group should be protected in known manner during the reaction with the hydrazine).

In the process according to the invention, the erythromycin imine of the general formula II is reacted with a substituted hydrazine of the general formula III chosen according to the desired substituents $R^{1A}$ and $R^2$.

The reaction is carried out in the presence of an acid. The desired acid may be provided by using the hydrazine compound in the form of a corresponding hydrazinium salt, for example a hydrazine hydrochloride or a hydrazinium sulphate. Alternatively, if the hydrazine compound is used in the form of a base, an acid should be added to the reaction mixture, suitably in an amount of at least one equivalent (with respect to the hydrazine compound).

The reaction may, for example, be carried out at a temperature within the range of from 0° C. to 60° C., conveniently at ambient temperature.

The reaction may be carried out in the presence of an inert solvent, which may be water or an organic solvent Suitable inert organic solvents include, for example, methanol, ethanol, tetrahydrofuran, dioxane, and dimethoxyethane. Water-miscible organic solvents may be used in admixture with water.

The hydrazine compound is suitably used in at least an equimolar amount with respect to the erythromycin 9-imine, advantageously in an amount of from 1 to 10 equivalents.

The immediate product of the reaction of the 9-imine compound of the general formula II with the hydrazine compound of the general formula III will be an N'-substituted erythromycin 9-hydrazone of the general formula IA. That product may then optionally be subjected to one or more various additional steps (a) to (f), in any suitable order, according to the desired product of the general formula I.

According to step (a) (i) above, if the desired product of the general formula I contains an N',11-O -methylene group which may be unsubstituted or substituted ($R^1+R^3$ denotes —CHR¹⁰—), the compound of the general formula IA may be reacted with an aldehyde of the general formula IV or a reactive derivative thereof to give a product of the general formula IB.

Suitable reactive derivatives of aldehydes or ketones of the general formula IV include, for example, acetals of the general formula VI:

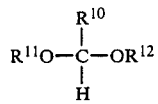    VI hemiacetals of the general formula VII:

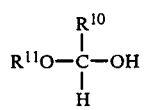    VII and enol ethers of the general formula VIII:

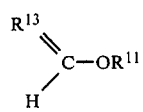    VIII in which formulae VI to VIII
$R^{10}$ is defined as above, each of $R^{11}$ and $R^{12}$, which may be identical or different, denotes a hydrocarbon group, advantageously a $(C_{1-6})$hydrocarbon group, preferably an alkyl group, especially a methyl or ethyl group; and $R^{13}$ denotes an optionally substituted divalent hydrocarbon or heterocyclyl group corresponding to an optionally substituted monovalent hydrocarbon or heterocyclyl group $R^{10}$ with the loss of a hydrogen atom on the carbon atom carrying the free valency.

The reaction according to step (a) (i) is suitably carried out in the presence of an acid catalyst. Preferred acid catalysts include pyridinium salts, for example pyridinium tosylate and pyridinium chloride. Other suitable acid catalysts include, for example, zinc chloride, cupric sulphate, boron trifluoride etherate, and organic sulphonic acids (for example, p-toluenesulphonic acid), optionally in conjunction with, for example, tertiary organic bases (for example, pyridine, dimethylpyridines, and trimethylpyridines).

Advantageously, the reaction is also carried out in the presence of a drying agent, for example anhydrous calcium sulphate, magnesium sulphate, sodium sulphate, cupric sulphate, or molecular sieves.

The reaction according to step (a) (i) may suitably be carried out in an inert solvent. Suitable solvents include, for example, ether solvents (for example, tetrahydrofuran, dioxan, ethoxyethane, and 1,2-dimethoxyethane), halogenated solvents (for example, chloroform and methylene chloride), and aromatic solvents (for example, toluene).

The reaction according to step (a) (i) may suitably be effected at a cool to slightly elevated temperature, preferably at ambient temperature. The reaction may, for example, be effected at a temperature within the range of from $-30°$ C. to $+30°$ C., preferably from $0°$ C. to $30°$ C., especially from $+10°$ C. to $+25°$ C.

When the compound of general formula I contains an unsubstituted $N',11$-O-methylene group ($R^1+R^3$ denotes $-CH_2-$), the compound of the general formula IA may be reacted with formaldehyde ($R^{10}$ denotes H in formula IV) to give a product of the general formula IB (in which $R^{10}$ denotes H). Such a reaction may be carried out in the presence of an inert solvent (for example those listed above), under mildly acid conditions (for example, pH 2 to pH 5), at a temperature of from $0°$ C. to $60°$ C., using at least one equivalent (advantageously from 1 to 50 equivalents) of formaldehyde.

According to step (a) (ii) above, the compound of the general formula IA, optionally containing protective groups, is reacted with a compound of the general formula V. In general formula V, each of X and Y, which may be identical to one another but are preferably different from one another, denotes a leaving group.

Examples of suitable leaving groups X and Y include halogen atoms (for example chlorine, bromine, and iodine), alkylsulphonyloxy groups (for example methanesulphonyloxy), and arylsulphonyloxy groups (for example p-toluenesulphonyloxy).

Preferably, each of X and Y denotes a halogen atom, especially different halogen atoms. More preferably X denotes chlorine or bromine and Y denotes bromine or iodine. A compound of the general formula V in which X denotes chlorine and Y denotes iodine is especially preferred.

The reaction according to step (a) (ii) is suitably carried out under strongly basic conditions. Examples of suitable strong bases include sodium hydride, potassium hydride, lithium amide, sodium amide, potassium amide, potassium t-butoxide, butyllithium, and lithium diisopropylamide.

The reaction according to step (a) (ii) may suitably be carried out in an inert solvent. Suitable solvents include, for example, polar aprotic solvents (for example, N,N-dimethylformamide, N,N-dimethylacetamide, dimethylsulphoxide, hexamethylphosphoric triamide, and N-methylpyrrolidinone and mixtures of two or more such solvents) and mixtures of one or more polar aprotic solvents with one or more ether solvents (for example, tetrahydrofuran, dioxan, ethoxyethane, and 1,2-dimethoxyethane)

The reaction according to step (a) (ii) may suitably be effected at a cool to ambient temperature preferably at a cool temperature. The reaction may, for example, be effected at a temperature within the range of from $-30°$ C. to $+30°$ C., preferably from $-5°$ C. to $+20°$ C., especially from $0°$ C. to $+15°$ C.

According to step (b) above, if the desired product of the general formula I is additionally N'-alkyl substituted ($R^1$ denotes $(C_{1-6})$alkyl), the N'-monosubstituted compound of the general formula IA or ID (in which $R^{14}$ or $R^1$ denotes hydrogen) may be subjected to reductive alkylation to give a product of the general formula IC. Such reductive alkylation may advantageously be effected by reaction with formaldehyde or a $(C_{1-5})$alkyl aldehyde in a hydrogen atmosphere in the presence of a transitional metal catalyst (for example, palladium on charcoal), under mildly acid conditions (for example, pH 3 to pH 5), at a temperature of from $0°$ C. to $30°$ C., in an organic solvent (for example, ethanol).

When the reductive alkylation is effected using formaldehyde, the product of the reductive methylation will generally be a mixture of a compound of the general formula IC (in which $R^{1B}$ denotes methyl) with a compound of the general formula IB (in which $R^{10}$ denotes hydrogen), typically in a ratio of approximately 1:1. The mixture thus obtained may be separated by conventional methods, such as by chromatography. If, however, such reductive methylation with formaldehyde is carried out on a compound of the general formula ID containing an 11,12-carbonate group, the 9,11-cyclisation cannot of course occur and the product will be only a compound of the general formula IC (in which $R^{1B}$ denotes methyl).

By way of a variation on the method described above, the reductive alkylation can be carried out on an erythromycin 9-hydrazone (see M. V. Sigal, Jr., et al and E. H. Massey et al, both op. cit) of the general formula IX:

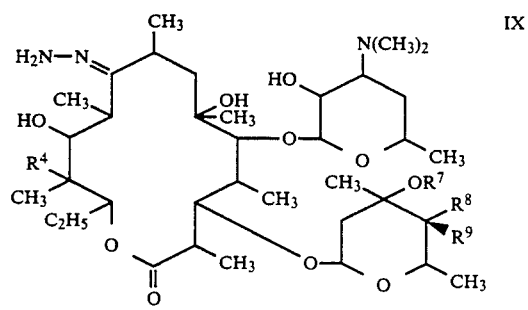

in which, $R^4$, $R^7$, $R^8$ and $R^9$ are defined as above, to give a compound of the general formula IC (in which $R^2$ denotes $(C_{1-6})$alkyl and $R^3$ denotes hydrogen), or when formaldehyde is used for the reductive alkylation, a mixture of compounds of the general formulae IB (in which $R^{10}$ denotes hydrogen) and IC (in which $R^{1B}$ and $R^2$ denote methyl and $R^3$ denotes hydrogen).

According to step (c) above, if the desired compound of the general formula I contains an 11,12-carbonate group ($OR^3 + R^4$ denote carbonate) the compound of the general formula IA or IC (in which $R^4$ denotes hydroxy and, in formula IC, $R^3$ denotes hydrogen) may be reacted with a reactive carbonyl compound to give a product of the general formula ID.

Examples of suitable reactive carbonyl compounds for introduction of the 11,12-carbonate group include phosgene $COCl_2$; oxalyl chloride $(COCl)_2$; carbonyl di-imidazole

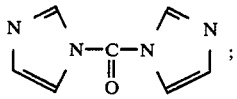

and aryl isocyanates, ArNCO (where Ar denotes an aryl group), which should preferably carry an electron-withdrawing substitutent on the aryl moiety, for example nitrophenylisocyanates and methylsulphonylphenylisocyanates. The reactive carbonyl compound may suitably be used in an excess of from 1 to 10 equivalents, based on the erythromycin compound.

The reactivity of the various reactive carbonyl compounds does vary and it is necessary to choose the reaction conditions accordingly.

In the case of the more reactive carbonyl compounds, phosgene and oxalyl chloride, for example, the reaction may conveniently be carried out at a temperature within the range of from $-50°$ to $+50°$ C., preferably from $-20°$ to $30°$ C., in an inert solvent. In the case of phosgene and oxalyl chloride, the reaction is preferably carried out in the presence of a weak base (e.g. triethylamine) as an acid acceptor: the presence of a catalytic amount of, for example, dimethylaminopyridine can also be advantageous.

In the case of carbonyl di-imidazole, for example, the reaction may conveniently be carried out at a temperature of from $0°$ to $150°$ C., preferably from $30°$ to $100°$ C., in an inert solvent. The reaction using carbonyl di-imidazole should preferably be carried out in the presence of a strong base, for example sodium hydride, which may conveniently be used in an amount of, say 2 equivalents (based on the erythromycin compound).

Suitable inert solvents for the reaction with the reactive carbonyl compounds include, for example, dichloromethane, chloroform, diethyl ether, tetrahydrofuran, dioxane, and dimethoxyethane (although the lower boiling solvents will not, of course, be suitable in cases where the reaction is carried out at higher temperatures).

With certain reagents, if the 4''-position has been left unprotected, substitution may occur at that position; for example, when using carbonyl di-imidazole, substitution of an imidazoylcarbonyl group can occur on the 4''-O-atom. Any such substituent may, if desired, readily be removed by displacement by an alcohol. For example, displacement by benzyl alcohol will give a 4''-benzyl carbonate derivative, and the 4''-hydroxy group may then be restored by hydrogenation in the manner discussed below. Alternatively, displacement by dihydric alcohol, for example, ethylene glycol can restore the 4''-hydroxy group directly.

According to step (d) above, and prior to or subsequent to any of the above-mentioned optional steps (a) to (c), the group(s) $R^8$ and $R^9$ may be converted to any other such group(s) denoted by $R^8$ and $R^9$ as defined above, by methods known in the art, for example by the methods disclosed in the above-cited references. For example, a compound in which $R^9$ denotes hydrogen and $R^8$ denotes hydroxy can be converted to a compound in which $R^8$ and $R^9$ together denote oxo and optionally thereafter to a compound in which $R^9$ denotes hydroxy or acetoxy and $R^8$ denotes hydrogen by methods analogous to those described in U.S. Pat. No. 3,884,903, op. cit.

According to step (e) above, and preferably after any subsequent optional steps (a) to (d), any protecting groups that may be present may be removed by a conventional method.

According to step (f) above, a compound of the general formula I may be converted to a pharmaceutically acceptable salt thereof or ester thereof in a conventional manner at any convenient stage in the manufacturing process, and in particular before or after step (d) and/or step (e) above.

Isolation and purification of a compound according to the invention may be carried out using conventional methods, and may include a chromatography step. Preferably the product is isolated in crystalline form.

The compounds according to the invention, that is to say, the compounds of the general formula I and their pharmaceutically acceptable salts and esters, have antibacterial properties and are useful for the treatment of bacterial infections in animals, especially mammals, including humans, in particular humans and domesticated animals (including farm animals). The compounds may be used for the treatment of infections caused by a wide range of gram-positive and gram-negative organisms including, for example, *Bacillus subtilis, Corynebacterium xerosis, Sarcina lutea, Staphylococcus aureus. Streptococcus faecalis, Streptococcus pyoqenes, Streptococcus aqalactiae, Streptococcus pneumoniae. Haemophilus sp. Neisseria sp., Chlamydia sp.,* and *Leqionella sp.*

The present invention provides a pharmaceutical composition comprising a compound according to the invention together with a pharmaceutically acceptable carrier or excipient.

The present invention also provides a method of treating bacterial infections in animals, especially in humans and in domesticated mammals, which comprises administering a compound or composition according to the invention to a patient in need thereof.

The compounds and compositions according to the invention may be formulated for administration in any convenient way for use in human or veterinary medicine, by analogy with other antibiotics.

The compounds and compositions according to the invention may be formulated for administration by any route, for example oral, topical or parenteral. The compositions may, for example, be made up in the form of tablets, capsules, powders, granules, lozenges, creams, syrups, or liquid preparations, for example solutions or suspensions, which may be formulated for oral use or in sterile form for parenteral administration by injection or infusion.

Tablets and capsules for oral administration may be in unit dosage form, and may contain conventional excipients including, for example, binding agents, for example syrup, acacia, gelatin, sorbitol, tragacanth, or polyvinylpyrollidone; fillers, for example lactose, sugar, maize-starch, calcium phosphate, sorbitol or glycine;

tabletting lubricants, for example magnesium stearate, talc, polyethylene glycol or silica; disintegrants, for example potato starch; and pharmaceutically acceptable wetting agents, for example sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or another suitable vehicle before use. Such liquid preparations may contain conventional additives, including, for example, suspending agents, for example sorbitol, methyl cellulose, glucose syrup, gelatin, hydroxyethyl cellulose, carboxymethyl cellulose, aluminium stearate gel or hydrogenated edible fats; emulsifying agents, for example lecithin, sorbitan monooleate or acacia; non-aqueous vehicles (which may include edible oils), for example almond oil, oily esters (for example glycerine), propylene glycol, or ethyl alcohol; preservatives, for example methyl or propyl p-hydroxybenzoate or sorbic acid; and, if desired, conventional flavouring and colouring agents.

A compound or composition according to the invention may suitably be administered to the patient in an antibacterially effective amount.

A composition according to the invention may suitably contain from 0.1% by weight, preferably from 10 to 60% by weight, of a compound according to the invention (based on the total weight of the composition), depending on the method of administration.

The compounds according to the invention may suitably be administered to the patient at a daily dosage of from 1.5 to 50 mg/kg of body weight. For an adult human (of approximately 70 kg body weight), from 100 to 3000 mg, for example about 1500 mg, of a compound according to the invention may be administered daily. Suitably, the dosage for adult humans is from 5 to 20 mg/kg per day. Higher or lower dosages may, however, be used in accordance with normal clinical practice.

When the compositions according to the invention are presented in unit dosage form, each unit dose may suitably comprise from 25 to 1000 mg, preferably from 50 to 500 mg, of a compound according to the invention.

No adverse toxicological effects are indicated when the compounds according to the invention are administered within the above-mentioned dosage ranges.

The following examples illustrate the preparation of compounds according to the present invention.

GENERAL PROCEDURES

Solutions were dried using anhydrous sodium sulphate. Solvents were removed by evaporation under reduced pressure using a rotary evaporator with bath temperature not exceeding 30° C. Unless stated otherwise, chromatography was performed on silica gel using 1:9:90 .880 $NH_3MeOH/CH_2Cl_2$ as eluent.

Starting materials

Erythromycin A 9-imine

Erythromycin A 9-oxime (2.0 g) in methanol (20 ml) was treated with ammonium acetate (5.0 g) and the mixture was stirred under nitrogen while titanium trichloride solution (5 ml) was added dropwise. After addition was complete, the mixture was stirred, under nitrogen, for a further 40 minutes. The mixture was then poured into chloroform (100 ml) and stirred while 10% potassium carbonate solution (60 ml) was added. The mixture was filtered, the solid being washed with more chloroform (2×20 ml). The layers of the filtrate were separated (the aqueous layer had pH 10–11). The chloroform solution was washed with water (2×50 ml) and was then dried ($Na_2SO_4$). The solvent was evaporated under reduced pressure to give erythromycin A 9-imine as a white foam (1.83 g).

Erythromycin A 9-hydrazone

Erythromycin A 9-hydrazone was prepared as described by M. V. Sigal, Jr., et al. *J.Amer.Chem.Soc.*, 1956, 78, 388.

EXAMPLE 1

Erythromycin A 9-semicarbazone

Erythromycin A 9-imine (200 mg) in 1,2-dimethoxyethane (2 ml) was treated with water (5 drops) and semicarbazide hydrochloride (33 mg). The mixture was stirred for 24h. It was then diluted with chloroform (30 ml) and washed with 10% potassium carbonate solution (20 ml) and water (2×20 ml). The solution was dried, the solvent was removed, and the resulting residue was chromatographed to give the title compound as a white solid (80 mg), $[\alpha]^{20}D = -22.8°$ (c 1.0, $CHCl_3$) FAB MS: m/z 813 ($MNa^+$).

EXAMPLE 2

Erythromycin A 9-phenylhydrazone

Using the same procedure as described in Example 1, but with phenylhydrazine hydrochloride (45 mg) in place of semicarbazide hydrochloride, the title compound was prepared as a pale yellow solid (60 mg). Found: $M^+$, 823.5197 ($C_{43}H_{73}N_3O_{12}$ requires M, 823.5194).

EXAMPLE 3

Erythromycin A 9-methylhydrazone

Erythromycin A 9-imine (280 mg) in methanol (3 ml) was treated with methylhydrazinium sulphate (65 mg) and triethylamine (30 mg). After 5h, the solution was diluted with ethyl acetate (30 ml) and was washed with 10% potassium carbonate solution (20 ml) and water (2×20 ml). The solution was dried and the solvent was removed to yield a white solid. Crystallisation from acetone/water gave the title compound as colourless crystals (220 mg), m.p. 128°–129° C., $[\alpha]^{20}D = -50.1°$ (c. 1.0, $CHCl_3$) Found: C, 59.75; H, 9.45; N, 5.25. $C_{38}H_{71}N_3O_{12}$ requires C, 59.9; H, 9.4; N, 5.5%.

EXAMPLE 4

Erythromycin A 9-(2-hydroxyethyl)hydrazone

Erythromycin A 9-imine (500 mg) and 2-hydroxyethylhydrazine (80 mg) was dissolved in 0.2M HCl in methanol (4 ml) After 20 h, the solution was diluted with ethyl acetate (50 ml) and was washed with 10% potassium carbonate solution (30 ml) and water (2×30 ml). The solution was dried, the solvent was removed, and the residue was chromatographed to give the title compound as a white solid (330 mg), $[\alpha]^{20}D = -44.5°$ (c. 1.0, $CHCl_3$). From acetone/water colourless crystals, m.p. 130°–131° C., were obtained. Found: $M^+$, 791.5169 ($C_{39}H_{73}N_3O_{13}$ requires M, 791.5143).

EXAMPLE 5

Erythromycin A 9-tetramethylenehydrazone

Erythromycin A 9-imine (200 mg) in methanol (2 ml) was treated with 1-aminopyrrolidine hydrochloride (40 mg) under nitrogen. After 19 h, the reaction was worked-up and chromatographed (as in Example 4) to give the title compound as a white solid (90 mg), $[\alpha]^{20}D = -160.0°$ (c. 1.0, CHCl$_3$); FAB MS: m/z 824 (MNa+).

EXAMPLE 6

Erythromycin A 9-(2-pyridyl)hydrazone

Erythromycin A 9-imine (200 mg) in methanol (2 ml) was treated with 2-hydrazinopyridine dihydrochloride (60 mg). After 22 h, the reaction was worked-up and chromatographed (as in Example 4) to give the title compound as a pale yellow gum (140 mg). Found: M+, 824.5172. (C$_{42}$H$_{72}$N$_4$O$_{12}$ requires M, 824.5147).

EXAMPLE 7

Erythromycin A 9-dimethylhydrazone and 9-(Z)-Erythromycin A 9-(N-methyl-N,11-O-methylene)hydrazone Erythromycin A 9-methylhydrazone (100 mg) in ethanol (12 ml)/acetate buffer (pH 4.8; 1 ml) was shaken with 10% palladium-on-charcoal (35 mg) and 37% formaldehyde (0.4 ml) under hydrogen (1 atmosphere) for 4 h. The catalyst was removed by filtration and was washed with ethanol and water. The ethanol was removed from the filtrate and the aqueous residue was basified (pH 11) using potassium carbonate and extracted with ethyl acetate. The solution was dried, the solvent was removed and the residue was chromatogaphed to give a mixture (ca. 1:1) of the title compounds as a white solid (80 mg).

EXAMPLE 8

Erythromycin A 9-[N-methyl-N-(2-hydroxyethyl)]hydrazone and 9-(Z)-Erythromycin A 9-[N-(2-hydroxyethyl)-N,11-O-methylene]hydrazone Erythromycin A 9-(2-hydroxyethyl)hydrazone (120 mg) was subjected to the process described in Example 7. On chromatography, erythromycin A 9-[N-methyl-N-(2-hydroxyethyl)]hydrazone was obtained as a colourless gum (70 mg), $[\alpha]^{23}D = -138°$ (c. 1.0, CHCl$_3$), FAB MS: m/z 828 (MNa+) and 9-(Z)-erythromycin A 9-[N-(2-hydroxyethyl)-N,11-O-methylene]hydrazone was also obtained as a colourless gum (40 mg), $[\alpha]^{22}D = -151.1°$ (c. 1.0, CHCl$_3$), FAB MS: m/z 826 (MNa+).

EXAMPLE 9

9-(Z)-Erythromycin A 9-[N-(2-hydroxyethyl)-N,11-O-methylene]hydrazone

Erythromycin A 9-(2-hydroxyethyl)hydrazone (200 mg) in tetrahydrofuran (5 ml) was treated with 37% formaldehyde (0.5 ml). After 2 h, the solution was diluted with ethyl acetate and was washed with dilute potassium carbonate solution and water (2x). The solution was dried and the solvent was removed to yield a white foam. The foam was dissolved in methanol (5 ml) and 2M HCl was added until the solution had pH 2. After 20 min, the mixture was diluted with ethyl acetate (50 ml) and was washed with 10% potassium carbonate (30 ml) and water (2×30 ml). The solution was dried, the solvent was removed, and the residue was chromatographed to give the title compound as a white solid (85 mg), $[\alpha]^{23}D = -155.8°$ (c. 1.0, CHCl$_3$).

EXAMPLE 10

Erythromycin A 9-dimethylhydrazone 11,12-carbonate

The reaction of Example 7 was repeated using 500 mg erythromycin A 9-methylhydrazone, and the product was chromatographed on silica gel using 1:9:190 0.880 NH$_3$/MeOH/Et$_2$O to give almost pure erythromycin A 9-dimethylhydrazone as a white foam (140 mg). This product was dissolved in dry tetrahydrofuran (5 ml) and the solution was treated with 50% sodium hydride dispersion in oil (25 mg) and the mixture was stirred for 5 min. Carbonyl diimidazole (200 mg) was then added and the mixture was stirred at 50° C. for 30 min. More sodium hydride (12 mg) and carbonyl diimidazole (80 mg) were added and stirring was continued at 50° C. for a further 45 min. The mixture was cooled to room temperature and benzyl alcohol (0.5 ml) was added. The mixture was stirred at 50° C. for 30 min. The mixture was cooled to room temperature, diluted with ethyl acetate, and washed with water. The solution was dried and the solvent was removed to yield a colourless gum. The gum was dissolved in ethanol (15 ml) and acetate buffer (pH 4.8, 1.5 ml) and the solution was shaken with 10% palladium-on-charcoal (50 mg) under hydrogen (1 atmosphere) for 2 h. The catalyst was removed by filtration and was washed with ethanol and water. The ethanol was removed from the filtrate under reduced pressure, and the residue was basified using sodium carbonate and extracted with ethyl acetate. The organic solution was dried and the solvent was removed to give a colourless gum. The gum was chromatographed on silica gel using 1.5:15:200 0.880 NH$_3$/MeOH/Et$_2$O to give the title compound as a white foam (70 mg), $[\alpha]^{20}D = -108.6°$ (c. 1.0, CHCl$_3$); FAB MS: m/z 824 (MNa+).

EXAMPLE 11

Erythromycin A 9-dimethylhydrazone and 9-(Z)-Erythromycin A 9-(N-methyl-N,11-O-methylene)hydrazone from Erythromycin A 9-hydrazone Erythromycin A 9-hydrazone (500 mg) in ethanol (20 ml), acetate buffer (pH 4.8, 1 ml) and 37% formaldehyde solution (1 ml) was shaken with 10% palladium-on-charcoal (50 mg) under hydrogen (1 atmosphere) for 3 h. Work-up and chromatography as in Example 7 gave a mixture of the two title compounds as a white solid, identical with that described in Example 7.

EXAMPLE 12

9-(Z)-Erythromycin A 9-(N-methyl-N,11-O-methylene)hydrazone

Erythromycin A 9-methylhydrazone (100 mg) in ethanol (4 ml) was treated with 37% formaldehyde solution (0.5 ml), acetic acid (0.5 ml), and 0.5M HCl (3 drops). The solution was kept for 2 h, and was then diluted with ethyl acetate (50 ml) and washed with 10% potassium carbonate (30 ml) and water (2×30 ml). The solution was dried, the solvent was removed, and the residue was chromatographed to give the title compound as a white foam (70 mg), mp 130°–133° C., $[\alpha]D^{22} -150.0°$ (c 1.0, CHCl$_3$). Found: C, 60.35; H, 9.45; N, 5.25. $C_{39}H_{71}N_3O_{12}$ requires C, 60.5; H, 9.25; N, 5.45%. Mass spectrum: M+, 773.5020. $C_{39}H_{71}N_3O_{12}$ requires M, 773.5038.

EXAMPLE 13

9-(Z)-Erythromycin A 9-(N-methyl-N,11-O-ethylidene)hydrazone

Using the process described in Example 12, but with acetaldehyde (0.3 ml) in place of 37% formaldehyde solution, erythromycin A 9-methylhydrazone (100 mg) was converted into the title compound. The product was obtained as colourless crystals (50 mg) from dichloromethane-hexane, mp 129°–132° C., $[\alpha]_D^{21} -178.4°$ (c 1.0, CHCl₃). Found: C, 60.95; H, 9.4; N, 5.0. $C_{40}H_{73}N_3O_{12}$ requires C, 60.95; H, 9.35; N, 5.35%. Mass spectrum: M+ 787.5184. $C_{40}H_{73}N_3O_{12}$ requires M, 787.5194.

EXAMPLE 14

Erythromycin A 9-(N-methyl)-ethylhydrazone

Erythromcyin A 9-methylhydrazone (180 mg) and acetaldehyde (0.5 ml) in ethanol (20 ml) containing an acetate buffer (pH 4.8; 2 ml) was shaken with 10% palladium-on-charcoal (60 mg) under hydrogen (1 atmosphere) for 5 hours. Work-up and chromatography as in Example 7 gave the title compound as a white solid (120 mg). From dichloromethane-hexane the product was obtained as colourless crystals, mp 126°–127° C., $[\alpha]_D^{21} -149.4°$ (c 1.0, CHCl₃). Found: C, 60.9; H, 9.8; N, 5.3. $C_{40}H_{75}N_3O_{12}$ requires C, 60.8; H, 9.55; N, 5.3%. Mass spectrum: M+, 789.5325. $C_{40}H_{75}N_3O_{12}$ requires M, 789.5351.

I claim:

1. A compound of the formula I, or a pharmaceutically acceptable ester or acid addition salt thereof:

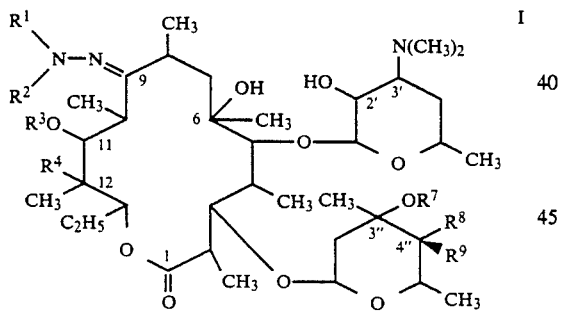

wherein $R^1$ is hydrogen or alkyl of up to 6 carbon atoms;
$R^2$ is alkyl of 1 to 6 carbon atoms unsubstituted or substituted by heterocyclyl of 5 or 6 ring members, amino, alkanoylamino of 1 to 6 carbon atoms in the alkyl moiety, mono-, di- or tri- alkylamino of 1 to 6 carbon atoms in each alkyl moiety, hydroxy, alkoxy of 1 to 6 carbon atoms, mercapto, alkylthio of 1 to 6 carbon atoms, heterocyclylthio of 5 or 6 ring members, phenylthio, sulphamoyl, carbamoyl, amidino, guanidino, nitro, chloro, bromo, fluoro, carboxy or a carboxyl salt or ester, alkanoyloxy of 1 to 6 carbon atoms in the alkyl moiety, phenylcarbonyloxy, heterocyclylcarbonyloxy of 5 or 6 ring members, acyl, alkenyl of 2 to 6 carbon atoms, alkynyl of 2 to 6 carbon atoms or phenyl or naphthyl; or $R^2$ is phenyl or naphthyl which is unsubstituted or substituted by up to three substituents selected from the group consisting of heterocyclyl of 5 or 6 ring members, amino, alkanoylamino of 1 to 6 carbon atoms in the alkyl moiety, mono-, di- or tri- alkylamino of 1 to 6 carbon atoms in each alkyl moiety, hydroxy, alkoxy of 1 to 6 carbon atoms, mercapto, alkylthio of 1 to 6 carbon atoms, heterocyclylthio of 5 or 6 ring members, phenylthio, sulphamoyl, carbamoyl, amidino, guanidino, nitro, chloro, bromo, fluoro, carboxy or a carboxyl salt or ester, alkanoyloxy of 1 to 6 carbon atoms in the alkyl moiety, phenylcarbonyloxy, heterocyclylcarbonyloxy of 5 or 6 ring members, acyl, halo, alkyl of 1 to 6 carbon atoms, phenyl, alkoxy of 1 to 6 carbon atoms, haloalkyl of 1 to 6 carbon atoms, hydroxy, amino, nitro, carboxy, alkoxycarbonyl of 1 to 6 carbon atoms, alkoxycarbonylalkyl of 1 to 6 carbon atoms in each of the alkoxy and allyl moieties, alkanoyloxy of 1 to 6 carbon atoms in the alkyl moiety or alkanoyl of 1 to 6 carbon atoms in the alkyl moiety; or $R^2$ is heterocyclyl of 5 or 6 ring members or carbamoyl;

$R^3$ is hydrogen;
$R^4$ is hydrogen or hydroxy; or
$R^1$ and $R^2$ together are straight-chain alkylene or alkenylene of 3 to 6 carbon atoms; or
$R^1$ and $R^3$ together are methylene unsubstituted or substituted by alkyl of 1 to 6 carbon atoms, phenyl, naphthyl, furyl, pyranyl, thienyl, dihydropyranyl or tetrahydrofuryl; or
$OR^3$ and $R^4$ together are carbonate; and
$R^7$ is hydrogen or methyl;
one of $R^8$ and $R^9$ is hydrogen, hydroxy, alkoxy of 1 to 6 carbon atoms, alkanoyloxy of 1 to 6 carbon atoms in the alkoxy moiety, amino, or a group of the formula $R^A$—SO₂—O—, in which
$R^A$ is a hydrocarbon, oxahydrocarbon, thiahydrocarbon or azahydrocarbon wherein the hydrocarbon is alkyl of 1 to 6 carbon atoms, alkenyl of 2 to 6 carbon atoms, phenyl, nitrophenyl, halophenyl, alkylphenyl, benzyl, nitrobenzyl, alkylbenzyl, phenoxyalkyl, nitrophenoxyalkyl or $R^G$—CH₂CH₂— wherein $R^G$ is amino, carbamoyl, sulphamoyl, alkoxy or alkylthio and wherein each of the above alkyl and alkoxy moieties is of 1 to 6 carbon atoms and the other of $R^8$ and $R^9$ is hydrogen, or $R^8$ and $R^9$ together are oxo, oxime, or acetyloxime.

2. A compound according to claim 1, in which $R^1$ and $R^3$ together are methylene.

3. A compound according to claim 1, wherein $R^1$ is methyl.

4. A compound according to claim 1, wherein $R^2$ is unsubstituted or substituted alkyl of 1 to 6 carbon atoms, or unsubstituted or substituted phenyl by up to three substitutents selected from the group consisting of heterocyclyl of 5 or 6 ring members, amino, alkanoylamino of 1 to 6 carbon atoms in the alkyl moiety, mono-, di- or tri-alkylamino of 1 to 6 carbon atoms in each alkyl moiety, hydroxy, alkoxy of 1 to 6 carbon atoms, mercapto, alkylthio of 1 to 6 carbon atoms, heterocyclylthio of 5 or 6 ring members, phenylthio, sulphamoyl, carbamoyl, amidino, guanidino, nitro, chloro, bromo, fluoro, carboxy or a carboxyl salt or ester, alkanoyloxy of 1 to 6 carbon atoms in the alkyl moiety, arylcarbonyloxy, heterocyclylcarbonyloxy of 5 or 6 ring members, acyl, thio, alkyl of 1 to 6 carbon atoms, phenyl, alkoxy of 1 to 6 carbon atoms, haloalkyl of 1 to 6 carbon atoms, hydroxy, amino, nitro, carboxy, alkoxycarbonyl of 1 to 6 carbon atoms, alkoxycarbonylalkyl of 1 to 6 carbon atoms in each of the alkoxy and alkyl moieties, alkanoyloxy of 1 to 6 carbon atoms in the alkyl moiety or alkanoyl of 1 to 6 carbon atoms in the alkyl moiety.

5. A compound according to claim 1 selected from the group consisting of:
(i) erythromycin A 9-semicarbazone;
(ii) erythromycin A 9-phenylhydrazone;
(iii) erythromycin A 9-methylhydrazone;
(iv) erythromycin A 9-(2-hydroxyethyl)hydrazone;
(v) erythromycin A 9-tetramethylenehydrazone;
(vi) erythromycin A 9-(2-pyridyl)hydrazone;
(vii) erythromycin A 9-dimethylhydrazone;
(viii) 9-(Z)-erythromycin A 9-(N-methyl-N,11-O-methylene)hydrazone;
(ix) erythromycin A 9-[N-methyl-N-(2-hydroxyethyl)]hydrazone;
(x) 9-(Z)-erythromycin A 9-[N-(2-hydroxyethyl)-N,11-O-methylene]hydrazone;
(xi) erythromycin A 9-dimethylhydrazone 11,12-carbonate;
(xii) 9-(Z)-erythromycin A 9-(N-methyl-N,11-O-methylene)hydrazone
(xiii) 9-(Z)-erythromycin A 9-(N-methyl-N,11-O-ethylidene)hydrazone and
(xiv) erythromycin A 9-(N-methyl)-ethylhydrazone or a
pharmaceutically acceptable ester or an acid addition salt thereof.

6. A pharmaceutical composition useful for treating bacterial infections in humans and animals which comprises an antibacterially effective amount of a compound of the formula I, or a pharmaceutically acceptable ester or acid addition salt thereof:

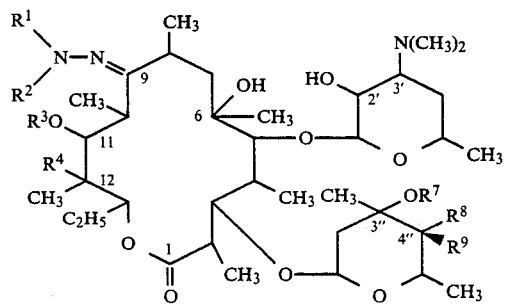

wherein
$R^1$ is hydrogen or alkyl of up to 6 carbon atoms;
$R^2$ is alkyl of 1 to 6 carbon atoms unsubstituted or substituted by heterocyclyl of 5 or 6 ring members, amino, alkanoylamino of 1 to 6 carbon atoms in the alkyl moiety, mono-, di- or tri- alkylamino of 1 to 6 carbon atoms in each alkyl moiety, hydroxy, alkoxy of 1 to 6 carbon atoms, mercapto, alkylthio of 1 to 6 carbon atoms, heterocyclylthio of 5 or 6 ring members, phenylthio, sulphamoyl, carbamoyl, amidino, guanidino, nitro., chloro, bromo, fluoro, carboxy or a carboxyl salt or ester, alkanoyloxy of 1 to 6 carbon atoms in the alkyl moiety, phenylcarbonyloxy, heterocyclylcarbonyloxy of 5 or 6 ring members, acyl, alkenyl of 2 to 6 carbon atoms, alkynyl of 2 to 6 carbon atoms or phenyl or naphthyl; or $R^2$ is phenyl or naphthyl which is unsubstituted or substituted by up to three substituents selected from the group consisting of heterocyclyl of 5 or 6 ring members, amino, alkanoylamino of 1 to 6 carbon atoms in the alkyl moiety, mono-, di- or tri- alkylamino of 1 to 6 carbon atoms in each alkyl moiety, hydroxy, alkoxy of 1 to 6 carbon atoms, mercapto, alkylthio of 1 to 6 carbon atoms, heterocyclylthio of 5 or 6 ring members, phenylthio, sulphamoyl, carbamoyl, amidino, guanidino, nitro, chloro, bromo, fluoro, carboxy or a carboxyl salt or ester, alkanoyloxy of 1 to 6 carbon atoms in the alkyl moiety, phenylcarbonyloxy, heterocyclylcarbonyloxy of 5 or 6 ring members, acyl, halo, alkyl of 1 to 6 carbon atoms, phenyl, alkoxy of 1 to 6 carbon atoms, haloalkyl of 1 to 6 carbon atoms, hydroxy, amino, nitro, carboxy, alkoxycarbonyl of 1 to 6 carbon atoms, alkoxycarbonylalkyl of 1 to 6 carbon atoms in each of the alkoxy and alkyl moieties, alkanoyloxy of 1 to 6 carbon atoms in the alkyl moiety or alkanoyl of 1 to 6 carbon atoms in the alkyl moiety; or $R^2$ is heterocycyl of 5 or 6 ring members;
$R^3$ is hydrogen;
$R^4$ is hydrogen or hydroxy; or
$R^1$ and $R^2$ together are straight-chain alkylene or alkenylene of 3 to 6 carbon atoms; or
$R^1$ and $R^3$ together are methylene unsubstituted or substituted by alkyl of 1 to 6 carbon atoms, phenyl, naphthyl, furyl, pyranyl, thienyl, dihydropyranyl or tetrahydrofuryl; or
$OR^3$ and $R^4$ together are carbonate; and
$R^7$ is hydrogen or methyl;
one of $R^8$ and $R^9$ hydrogen, hydroxy, alkoxy of 1 to 6 carbon atoms, alkanoyloxy of 1 to 6 carbon atoms in the alkoxy moiety, amino, or a group of the formula $R^A$—$SO_2$—O—, in which
$R^A$ is a hydrocarbon, oxahydrocarbon, thiahydrocarbon or azahydrocarbon wherein the hydrocarbon is alkyl of 1 to 6 carbon atoms, alkenyl of 2 to 6 carbon atoms, phenyl, nitrophenyl, halophenyl, alkylphenyl, benzyl, nitrobenzyl, alkylbenzyl, phenoxyalkyl, nitrophenoxyalkyl or $R^G$—$CH_2CH_2$— wherein $R^G$ is amino, carbamoyl, sulphamoyl, alkoxy or alkylthio and wherein each of the above alkyl and alkoxy moieties is of 1 to 6 carbon atoms; and the other of $R^8$ and $R^9$ is hydrogen, or $R^8$ and $R^9$ together are oxo, oxime, or acetyloxime, in combination with a pharmaceutically acceptable carrier.

7. A composition according to claim 6 in which $R^1$ and $R^3$ together are methylene.

8. A composition according to claim 6 wherein is methyl.

9. A composition according to claim 6 wherein $R^2$ is unsubstituted or substituted alkyl of 1 to 6 carbon atoms, or unsubstituted or substituted phenyl by up to three substitutents selected from the group consisting of heterocyclyl of 5 or 6 ring members, amino, alkanoylamino of 1 to 6 carbon atoms in the alkyl moiety, mono-, di- or tri-alkylamino of 1 to 6 carbon atoms in each alkyl moiety, hydroxy, alkoxy of 1 to 6 carbon atoms, mercapto, alkylthio, of 1 to 6 carbon atoms, heterocyclylthio of 5 or 6 ring members, phenylthio, sulphamoyl, carbamoyl, amidino, guanidino, nitro, chloro, bromo, fluoro, carboxy or a carboxyl salt or ester, alkanoyloxy of 1 to 6 carbon atoms in the alkyl moiety, arylcarbonyloxy, heterocyclylcarbonyloxy of 5 or 6 ring members, acyl, halo, alkyl of 1 to 6 carbon atoms, phenyl, alkoxy of 1 to 6 carbon atoms, haloalkyl of 1 to 6 carbon atoms, hydroxy, amino, nitro, carboxy, alkoxycarbonyl of 1 to 6 carbon atoms, alkoxycarbonylalkyl of 1 to 6 carbon atoms in each of the alkoxy and alkyl moieties, alkanoyloxy of 1 to 6 carbon atoms in the alkyl moiety or alkanoyl of 1 to 6 carbon atoms in the alkyl moiety.

10. A method of treating bacterial infections in humans and animals which comprises administering to a human or animal in need thereof an antibacterially effective amount of a compound of the formula I, or a pharmaceutically acceptable ester or acid addition salt thereof

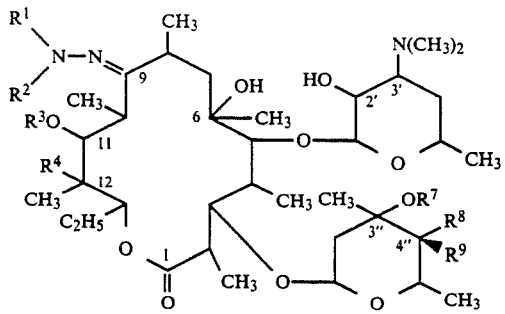

wherein
$R^1$ is hydrogen or alkyl of up to 6 carbon atoms;
$R^2$ is alkyl of 1 to 6 carbon atoms unsubstituted or substituted by heterocyclyl of 5 or 6 ring members, amino, alkanoylamino of 1 to 6 carbon atoms in the alkyl moiety, mono-, di or tri- alkylamino of 1 to 6 carbon atoms in each alkyl moiety, hydroxy, alkoxy of 1 to 6 carbon atoms, mercapto, alkylthio of 1 to 6 carbon atoms, heterocyclylthio of 5 or 6 ring members, phenylthio, sulphamoyl, carbamoyl, amidino, guanidino, nitro, chloro, bromo, fluoro, carboxy or a carboxyl salt or ester, alkanoyloxy of 1 to 6 carbon atoms in the alkyl moiety, phenylcarbonyloxy, heterocyclylcarbonyloxy of 5 or 6 ring members, acyl, alkenyl of 2 to 6 carbon atoms, alkynyl of 2 to 6 carbon atoms or phenyl or naphthyl; or $R^2$ is phenyl or naphthyl which is unsubstituted or substituted by up to three substituents selected from the group consisting of heterocyclyl of 5 or 6 ring members, amino, alkanoylamino of 1 to 6 carbon atoms in the alkyl moiety, mono-, di- or tri- alkylamino of 1 to 6 carbon atoms in each alkyl moiety, hydroxy, alkoxy of 1 to 6 carbon atoms, mercapto, alkylthio of 1 to 6 carbon atoms, heterocyclylthio of 5 or 6 ring members, phenylthio, sulphamoyl, carbamoyl, amidino, guanidino, nitro, chloro, bromo, fluoro, carboxy or a arboxyl salt or ester, alkanoyloxy of 1 to 6 carbon atoms in the alkyl moiety, phenylcarbonyloxy, heterocyclylcarbonyloxy of 5 or 6 ring members, acyl, halo, alkyl of 1 to 6 carbon atoms, phenyl, alkoxy of 1 to 6 carbon atoms, haloalkyl of 1 to 6 carbon atoms, hydroxy, amino, nitro, carboxy, alkoxycarbonyl of 1 to 6 carbon atoms, alkoxycarbonylalkyl of 1 to 6 carbon atoms in each of the alkoxy and alkyl moieties, alkanoyloxy of 1 to 6 carbon atoms in the alkyl moiety or alkanoyl of 1 to 6 carbon atoms in the alkyl moiety; or $R^2$ is heterocyclyl of 5 or 6 ring members;
$R^3$ is hydrogen;
$R^4$ is hydrogen or hydroxy;
or
$R^1$ and $R^2$ together are straight-chain alkylene or alkenylene of 3 to 6 carbon atoms; or $R^1$ and $R^3$ together are methylene unsubstituted or substituted by alkyl of 1 to 6 carbon atoms, phenyl, naphthyl, furyl, pyranyl, thienyl, dihydropyranyl, or tetrahydrofuryl; or
$OR^3$ and $R^4$ together are carbonate; and
$R^7$ is hydrogen or methyl;
one of $R^8$ and $R^9$ hydrogen, hydroxy, alkoxy of 1 to 6 carbon atoms, alkanoyloxy of 1 to 6 carbon atoms in the alkoxy moiety, amino, or a group of the formula $R^A$—$SO_2$—O—, in which $R^A$ is a hydrocarbon, oxahydrocarbon, thiahydrocarbon or azahydrocarbon wherein the hydrocarbon is alkyl of 1 to 6 carbon atoms, alkenyl of 2 to 6 carbon atoms, phenyl, nitrophenyl, halophenyl, alkylphenyl, benzyl, nitrobenzyl, alkylbenzyl, phenoxyalkyl, nitrophenoxyalkyl or $R^G$—$CH_2CH_2$— wherein $R^G$ is amino, carbamoyl, sulphamoyl, alkoxy or alkylthio and wherein each of the above alkyl and alkoxy moieties is of 1 to 6 carbon atoms; and the other of $R^8$ and $R^9$ is hydrogen, or $R^8$ and $R^9$ together are oxo, oxime, or acetyloxime, in combination with a pharmaceutically acceptable carrier, in combination with a pharmaceutically acceptable carrier.

11. A method according to claim 10 in which $R^1$ and $R^3$ together are methylene.

12. A method according to claim 10 wherein $R^1$ is methyl.

13. A method according to claim 10 wherein $R^2$ is unsubstituted or substituted alkyl of 1 to 6 carbon atoms, or unsubstituted or substituted phenyl by up to three substituents selected from the group consisting of heterocyclyl of 5 or 6 ring members, amino, alkanoylamino of 1 to 6 carbon atoms in the alkyl moiety, mono-, di- or tri- alkylamino of 1 to 6 carbon atoms in each alkyl moiety, hydroxy, alkoxy of 1 to 6 carbon atoms, mercapto, alkylthio of 1 to 6 carbon atoms, heterocyclylthio of 5 or 6 ring members, phenylthio, sulphamoyl, carbamoyl, amidino, guanidino, nitro, chloro, bromo, fluoro, carboxy or a carboxyl salt or ester, alkanoyloxy of 1 to 6 carbon atoms in the alkyl moiety, arylcarbonyloxy, heterocyclylcarbonyloxy of 5 or 6 ring members, acyl, halo, alkyl of 1 to 6 carbon atoms, phenyl, alkoxy of 1 to 6 carbon atoms, haloalkyl of 1 to 6 carbon atoms, hydroxy, amino, nitro, carboxy, alkoxycarbonyl of 1 to 6 carbon atoms, alkoxycarbonylalkyl of 1 to 6 carbon atoms in each of the alkoxy and alkyl moieties, alkanoyloxy of 1 to 6 carbon atoms in the alkyl moiety or alkanoyl of 1 to 6 carbon atoms in the alkyl moiety.

14. A pharmaceutical composition according to claim 6, wherein the compound is selected from the group consisting of:
(i) erythromycin A 9-semicarbazone;
(ii) erythromycin A 9-phenylhydrazone;
(iii) erythromycin A 9-methylhydrazone;
(iv) erythromycin A 9-(2-hydroxyethyl)hydrazone;
(v) erythromycin A 9-tetramethylenehydrazone;
(vi) erythromycin A 9-(2-pyridyl)hydrazone;
(vii) erythromycin A 9-dimethylhydrazone;
(viii) 9-(Z)-erythromycin A 9-(N-methyl-N,11-O-methylene)hydrazone;
(ix) erythromycin A 9-[-methyl-N-(2-hydroxyethyl)-]hydrazone;
(x) 9-(Z)-erythromycin A 9-[-(2-hydroxyethyl)-N,11-O-methylene]hydrazone;
(xi) erythromycin A 9-dimethylhydrazone 11,12-carbonate;
(xii) 9-(Z)-erythromycin A 9-(N-methyl-N,11-O-methylene)hydrazone (xiii) 9-(Z)-erythromycin A 9-(N-methyl-N,11-O-ethylidene)hydrazone and (xiv) erythromycin A 9-(N-methyl)-ethylhydrazone or a pharmaceutically acceptable ester or an acid addition salt thereof.

15. A method according to claim 10, wherein the compound is selected from the group consisting of:

(i) erythromycin A 9-semicarbazone;

(ii) erythromycin A 9-phenylhydrazone;

(iii) erythromycin A 9-methylhydrazone;

(iv) erythromycin A 9-(2-hydroxyethyl)hydrazone;

(v) erythromycin A 9-tetramethylenehydrazone;

(vi) erythromycin A 9-(2-pyridyl)hydrazone;

(vii) erythromycin A 9-dimethylhydrazone;

(viii) 9-(Z)-erythromycin A 9-(N-methyl-N,11-O-methylene)hydrazone;

(ix) erythromycin A 9-[N-methyl-N-(2-hydroxyethyl)]hydrazone;

(x) 9-(Z)-erythromycin A 9-[N-(2-hydroxyethyl)N,11-O-methylene]hydrazone;

(xi) erythromycin A 9-dimethylhydrazone 11,12-carbonate;

(xii) 9-(Z)-erythromycin A 9-(N-methyl-N,11-O-methylene)hydrazone (xiii) 9-(Z)-erythromycin A 9-(N-methyl-N,11-O-ethylidene)hydrazone and (xiv) erythromycin A 9-(N-methyl)-ethylhydrazone or a pharmaceutically acceptable ester or an acid addition salt thereof.

* * * * *